United States Patent [19]

Perry et al.

[11] Patent Number: 5,282,857
[45] Date of Patent: Feb. 1, 1994

[54] GEL-FILLED IMPLANTS

[76] Inventors: Larry C. Perry, 3333 Country Ridge Dr., Antioch, Tenn. 37013; G. Patrick Maxwell, 4415 Gerald Pl., Nashville, both of Tenn. 37205

[21] Appl. No.: 867,417

[22] Filed: Apr. 13, 1992

[51] Int. Cl.⁵ .......................... A61F 2/12; A61F 2/02
[52] U.S. Cl. ............................................ 623/8; 623/11
[58] Field of Search ................ 623/7, 8, 11, 12, 16, 623/66

[56] References Cited

U.S. PATENT DOCUMENTS

| | | | |
|---|---|---|---|
| 4,292,300 | 9/1981 | Byrne et al. | 604/288 |
| 4,455,143 | 6/1984 | Theeuwes et al. | 604/890.1 |
| 4,563,182 | 1/1986 | Stoy et al. | 604/285 |
| 4,601,893 | 7/1986 | Cardinal | 604/890.1 |
| 4,605,691 | 8/1986 | Balazs et al. | 524/27 |
| 4,731,081 | 3/1988 | Tiffany et al. | 623/8 |
| 4,743,248 | 5/1988 | Bartoo et al. | 604/890.1 |
| 4,781,714 | 11/1988 | Eckenhoff et al. | 604/890.1 |
| 4,819,617 | 4/1989 | Goldberg et al. | 623/6 |
| 4,904,260 | 2/1990 | Ray et al. | 623/17 |
| 4,955,881 | 9/1990 | Eckenhoff | 604/890.1 |
| 4,957,494 | 9/1990 | Wong et al. | 604/891.1 |
| 5,008,102 | 4/1991 | York | 623/6 |
| 5,067,965 | 11/1991 | Ersek et al. | 623/66 |
| 5,116,370 | 5/1992 | Foglietti | 623/8 |
| 5,116,371 | 5/1992 | Christensen et al. | 623/8 |
| 5,123,923 | 6/1992 | Pommier et al. | 623/16 |
| 5,192,326 | 3/1993 | Bao et al. | 623/17 |

*Primary Examiner*—David Isabella
*Attorney, Agent, or Firm*—Renner, Otto, Boisselle & Sklar

[57] ABSTRACT

This invention relates to a medical implant, which comprises an outer envelope and a gel filler material, wherein the gel comprises water and a cellulose gelling agent. The gel in the implant may further contain a lubricating agent. The components of the gel are a biocompatible and do not adversely affect human beings. Implants containing the lubricating agent have a decreased tendency of failure caused by internal friction on the envelope. The implants of the present invention have similar characteristics of the human breast.

16 Claims, No Drawings

GEL-FILLED IMPLANTS

TECHNICAL FIELD OF THE INVENTION

This invention relates to medical prostheses, especially those used for a breast or a testicular prosthesis.

BACKGROUND OF THE INVENTION

The reconstruction or cosmetic variation of a breast, such is often performed following mastectomy, has become an increasingly frequent surgical procedure. The development and use of silicon-gel and silicon-filled implants have contributed to the popularity of this procedure. Recent concern over the effects of the filler of these implants, e.g. silicon-gel, on the health of women has lead to a decrease in their use.

Therefore, it is desirable to provide a filler material for an implant which simulates or duplicates the characteristics of a natural breast. Further, it is desirable to provide a material that does not have an adverse effect on the human body containing the implants.

U.S. Pat. No. 4,772,284 relates to a breast prosthesis with improved biocompatibility and methods of making the same. The breast prosthesis is a single lumen implantable and biocompatible breast prosthesis composed of an outer membrane of silastic, medical grade silicon, and an inner material selected from the group consisting of purified reconstructive collagen gel and a purified gel of polyalpha amino homopolymers or random copolymers having a molecular weight of from 5,000 to 400,000.

U.S. Pat. No. 4,787,905 relates to gel for breast prosthesis. The gel is a mixture of hydroxy-terminated polybutadiene resin, diundecylphthalate, polymethylenepolyphenyl isocyanate, and dibutyltin dilaurate catalyst, wherein the mixture is cured to form the gel.

U.S. Pat. No. 4,790,848 relates to a breast prosthesis with multiple lumens. The implant comprises an inner lumen of substantially spherical shape. The inner lumen is unattached, or free-floating. The lumens are filled with silicon gel or similar fluid material.

U.S. Pat. No. 4,995,885 relates to a radiolucent breast implant. The radiolucent breast implant is composed of a silicon envelope filled with any biocompatible triglyceride such as peanut oil or sunflower oil or any other material having an effective atomic number of 5.9, which is the effective atomic number of fat. This breast implant is radiolucent in that it duplicates the photoelectric interference of fat which is the major effect producing subject at low radiation levels as used in mammography.

SUMMARY OF THE INVENTION

This invention relates to a medical implant, comprising an outer envelope and a gel filler material, wherein the gel comprises water and a cellulose gelling agent. The gel in the implant may further contain a lubricating agent. The invention also relates to a method of augmenting or reconstructing a human breast comprising the steps of subcutaneously implanting a medical implant, comprising an outer envelope and a gel filler material, wherein the gel comprises water and a cellulose gelling agent into a human body. In another aspect, the invention relates to a method of preparing medical implants comprising the steps of filling an outer envelope of a medical-grade elastomer with a gel filler material, wherein the gel comprises water and a cellulose gelling agent, and sealing the envelope to form a medical implant. The components of the gel are preferably biocompatible so as not adversely to affect human beings. Implants containing the lubricating agent have a decreased tendency of failure caused by internal friction on the envelope. The implants of the present invention have similar characteristics to the human breast. These implants may be used for breast augmentation or reconstruction.

DETAILED DESCRIPTION OF THE INVENTION

As used in the specification and appended claims, the use of the term "gel" refers to gelatinous and "jelly-like" materials which provide the physical characteristics of the medical implants of the present invention.

The implants of the present invention may be used as an implant anywhere in the human body, especially as replacements for breasts and testicles. These implants are also useful for augmentation of the breasts. It should be recognized that the characteristics of the implant may be altered by altering the density of the gel of the implant. In one embodiment, the density of the gel of the implant approximates that of the human breast. The gel of the implant generally has a density from about 0.8, or about 0.9, or about 0.95 up to about 1.5, or to about 1.4, or to about 1.3 or to about 1.2.

The implant is comprised of an outer envelope. The envelope is generally a medical-grade elastomeric material. An example of a particularly useful envelope is a silicon envelope.

The filler material of the implants comprises a gel formed from water and a cellulose thickening agent. The water is generally present in a major amount, usually an amount greater than 70%, or about 75%, or about 80% by weight of the gel. In one embodiment, the water is present in an amount from about 80%, or about 85% up to about 95%, or about 93% by weight of the gel. The water is preferably purified and sterile as is known to those in the art.

The cellulose thickening agent or cellulose derivative provides thickening of the water to form the gel of the present invention. As is known, cellulose is a polymer of glucose rings derived from plants. In one embodiment, the cellulose thickening agent is a cellulose ether. Examples of cellulose thickening agents include methylcellulose, ethylcellulose, hydroxyethylcellulose, hydroxypropylcellulose, hydroxyethyl, ethylcellulose, sodium carboxymethylcellulose, and sodiumcarboxymethyl, hydroxyethylcellulose. Preferably, the cellulose thickening agent is hydroxyethylcellulose, hydroxypropylcellulose or methylcellulose, more preferably methylcellulose.

The cellulose thickening agent is present in an amount sufficient to gel the water. In one embodiment, the cellulose thickening agent is present in an amount to produce a density which approximates the density of the human breast. The cellulose thickening agent is generally present in an amount from about 0.5%, or about 1%, up to about 15%, or to about 10%, or to about 8% by weight of the gel.

In one embodiment, the gel further comprises a lubricating agent. The lubricating agent can be any agent which reduces the internal friction in the envelope. The lubricating agent may be a polyol. Examples of useful polyols include ethyleneglycol, propyleneglycol, butanetriol, butanediol, hexanediol, hexanetriol and the like. Preferably, the lubricating agent is glycerol or propyleneglycol. In another embodiment, the lubricating agent may be any glyceride, preferably a triglyceride. Examples of glyceride lubricants include coconut triglycerides, and oleyltriglycerides.

In addition to the water, cellulose thickening agents and optionally lubricating agents, the gel may additionally contain other additives which act as preservatives, antioxidants, pH controlling agents and antibacterial agents in the gel. Examples of these agents include methylparaben, propylparaben, sodium hydroxide, glucono delta lactate, chlorhexidine gluconate, propyleneoxide and the like.

In one embodiment, the lubricants of the present invention may be commercially available surgical and personal lubricant gels. Examples of these gels include Surgilube® surgical lubricant available commercially from E. Fougera & Company, HR® Lubricating Jelly available commercially from Carter-Wallace, Inc. and K-Y Lubricating Jelly available commercially from Johnson & Johnson.

As described above the implants of the present invention may be used as replacements for body tissues or augmentation of body tissues. In one embodiment, the implants are used for breast reconstruction and/or augmentation. The process for using the implants involves placing the implants of the present invention subcutaneously in a human being in a region where replacement and/or augmentation is desired. For instance, for breast augmentation, the implant is subcutaneously placed into the breast region. The process for placing the implant into a human is known to those skilled in the art and generally involved inserting the implant through an incision in the chest. Methods of placing implants is known to those in the art.

The invention further comprises the process of preparing medical implants which involves the steps of filling an outer envelope of a medical grade elastomer with a gel as described herein. The envelope is sealed to form the medical implant. The sealing procedure is known to those skilled in the art.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A sealed implantable prosthesis for implantation into soft tissue for replacing or augmenting the tissues, comprising an outer envelope forming a hollow sealed shell defining an enclosed volume, said hollow shell being filled with a gel filler with predetermined density which is a mixture of water and of a cellulose derivative selected from the group consisting of methylcellulose, ethylcellulose, hydroxyethylcellulose, hydroxypropylcellulose, hydroxyethyl, ethylcellulose, sodium caroboxymethylcellulose, and sodium carboxymethyl, hydroxyethylcellulose and which is retained in said sealed shell to maintain constant its predetermined density.

2. An implantable prosthesis according to claim 1, wherein said water is present in the gel in an amount greater than 70% by weight of the gel.

3. An implantable prosthesis according to claim 2, wherein the water is present in an amount of 75% to about 95% by weight of the gel.

4. An implantable prosthesis according to claim 2, wherein said cellulose derivative is present in an amount of 0.5% to about 15% by weight of the gel.

5. An implantable prosthesis according to claim 1, wherein the water is present in the gel in a major amount so that the volume of the gel is determined substantially by the volume of the water.

6. An implantable prosthesis according to claim 1, wherein the gel essentially consists of a mixture of water and of the cellulose derivative.

7. An implantable prosthesis according to claim 2, wherein the cellulose derivative is present in an amount from about 0.5% to about 8% by weight of gel.

8. An implantable prosthesis according to claim 1, wherein the gel has a density from about 0.8 to about 1.5 $g/cm_3$.

9. The implant of claim 1 wherein the cellulose cellulose derivative is hydroxyethylcellulose, hydroxypropylcellulose or methylcellulose.

10. The implant of claim 1 wherein the envelope is a medical-grade elastomer.

11. The implant of claim 1 wherein the envelope is a medical-grade silicon.

12. The implant of claim 1 further comprising a lubricating agent.

13. The implant of claim 12 wherein the lubricating agent is a polyol lubricating agent.

14. The implant of claim 12 wherein the lubricating agent is propyleneglycol or glycerol.

15. A method of augmenting or reconstructing a human breast, comprising the steps of subcutaneously implanting a sealed medical prosthesis into a human being, wherein the prosthesis comprises an outer envelope forming a hollow sealed shell defining an enclosed volume and a gel filler with predetermined density in said outer envelope, wherein the gel is a mixture of water and a cellulose gelling agent selected from the group consisting of methylcellulose, ethylcellulose, hydroxyethylcellulose, hydroxypropylcellulose, hydroxyethyl, ethylcellulose, sodium caroboxymethylcellulose, and sodium carboxymethyl, hydroxyethylcellulose, and wherein said shell is sealed to contain the gel within the medical prostheses and maintain constant said predetermined density.

16. A method of preparing medical implantable completely sealed prostheses, comprising the steps of mixing water and a cellulose derivative selected from the group consisting of methylcellulose, ethylcellulose, hydroxyethylcellulose, hydroxypropylcellulose, hydroxyethyl, ethylcellulose, sodium caroboxymethylcellulose, and sodium carboxymethyl, hydroxyethylcellulose to form a gel filler with predetermined density in which water is present in a major amount, filling with said gel filler an outer envelope of a medical-grade elastomer forming a hollow shell providing a substantially sealed internal surface to the gel, and sealing the outer envelope to form a medical implantable prosthesis in which the gel filter is retained and its predetermined density is maintained constant within the sealed envelope.

* * * * *

UNITED STATES PATENT AND TRADEMARK OFFICE
CERTIFICATE OF CORRECTION

PATENT NO. : 5,282,857
DATED : February 1, 1994
INVENTOR(S) : Larry C. Perry and G. Patrick Maxwell It is certified that error appears in the above-indentified patent and that said Letters Patent is hereby corrected as shown below:

Column 3, line 13, change "lubricants" to --implants--.

Signed and Sealed this

Thirtieth Day of April, 1996

Attest:

BRUCE LEHMAN

*Attesting Officer*      *Commissioner of Patents and Trademarks*